(12) United States Patent
Musson, IV

(10) Patent No.: US 8,546,360 B2
(45) Date of Patent: Oct. 1, 2013

(54) METHOD OF TREATING CITRUS PLANTS TO REDUCE BACTERIAL INFECTIONS

(75) Inventor: George Hauley Musson, IV, Raleigh, NC (US)

(73) Assignee: Bayer CropScience LP, Research Triangle Park, NC (US)

( * ) Notice: Subject to any disclaimer, the term of this patent is extended or adjusted under 35 U.S.C. 154(b) by 164 days.

(21) Appl. No.: 12/918,230

(22) PCT Filed: Feb. 12, 2009

(86) PCT No.: PCT/US2009/033854
§ 371 (c)(1),
(2), (4) Date: Sep. 20, 2010

(87) PCT Pub. No.: WO2009/131735
PCT Pub. Date: Oct. 29, 2009

(65) Prior Publication Data
US 2011/0021463 A1    Jan. 27, 2011

Related U.S. Application Data

(60) Provisional application No. 61/125,039, filed on Apr. 22, 2008.

(51) Int. Cl.
*A01N 57/18* (2006.01)
(52) U.S. Cl.
USPC ........................................................ 514/141
(58) Field of Classification Search
None
See application file for complete search history.

(56) References Cited

U.S. PATENT DOCUMENTS

| 5,206,228 A | 4/1993 | Collins |
| 6,375,965 B1 | 4/2002 | Matsuo et al. |

FOREIGN PATENT DOCUMENTS

| EP | 0249566 | 12/1987 |
| IL | 82311 | 6/1992 |
| WO | 01/28334 | 4/2001 |
| WO | 01/28335 | 4/2001 |

OTHER PUBLICATIONS

International Search Report for PCT/US09/33854, Filed Feb. 12, 2009.
European Search Report based on Application No. 09733685.3-2103/2288262 PCT/US2009033854 mailed Oct. 19, 2012.
Gold et al.; "Identifying Insect Vectors and Transmission Mechanisms for Banana Xantomonas Wilt"; Crop Protection Program, R8484, Final Technical Report; January 25, 2006; pp. 1-36.
Hall et al.: "Toxicity of Pesticides to Tamarixia Radiata, A Parasitoid of the Asian Citrus Psyllid"; Biocontrol, Kluwer Academic Publishers, DO; vol. 55; No. 5; May 23, 2010; pp. 601-611.
Alvarez et al.; "Comparison of Application Methods of Systemic Fungicides to Suppress Branch Canker in Clementine Trees Caused by Phytophthora Citrophthora"; Plant Disease; Vol. 92; No. 9; September 1, 2008; p. 1357-1363.

*Primary Examiner* — Kortney L Klinkel

(57) ABSTRACT

A method of treating a citrus plant is provided to reduce the incidence of one or more insect-vectored bacterial infections such as citrus greening. The method comprises the step of applying a treatment composition one or more times to the plant, wherein the treatment composition comprises an effective amount of aluminum tris(O-ethyl phosphonate).

19 Claims, No Drawings

METHOD OF TREATING CITRUS PLANTS TO REDUCE BACTERIAL INFECTIONS

CROSS-REFERENCE TO RELATED APPLICATIONS

This application is national stage entry of PCT/US09/33854 filed Feb. 12, 2009, which claims Priority from Provisional Application 61/125,039, filed Apr. 22, 2008.

FIELD OF THE INVENTION

The present invention is directed to methods of improving citrus plant growth by reducing the incidence of insect-vectored bacterial infections.

BACKGROUND OF THE INVENTION

Problems with insect-vectored bacterial diseases in plants such as commercial crops are well known and documented. There is often a serious problem with yield loss due to the lack of effective disease prevention or control measures, particularly for new strains of infectious diseases.

According to the United State Department of Agriculture, citrus greening, also called Huanglongbing or yellow dragon disease, is one of the more serious diseases of citrus. This bacterial disease is thought to have originated in China in the early 1900's. The disease is primarily spread by two species of psyllid insects. One species, the Asian citrus psyllid, *Diaphorina citri*, has been present in Florida since 1998. The bacteria itself is not harmful to humans but the disease has harmed trees in Asia, Africa, the Arabian Peninsula, and Brazil. There are three strains of the bacteria: an Asian version, an African version, and a recently described American strain discovered in Brazil.

The Asian strain, *Candidatus Liberibacter asiaticus*, was found in Florida in early September, 2005. As a result, citrus greening disease is becoming a major threat to the U.S. citrus industry. Other than tree removal, there has been no known effective control once a tree is infected and there has been no known cure for the disease. Infected trees may produce misshapen, unmarketable, bitter fruit. Citrus greening reduces the quantity and quality of citrus fruits, eventually rendering infected trees useless. In areas of the world affected by citrus greening the average productive lifespan of citrus trees has dropped from 50 or more years to 15 or less. The trees in the orchards usually die 3-5 years after becoming infected and require removal and replanting. An infected tree produces fruit that is unsuitable for sale as fresh fruit or for juice.

Citrus plants infected by the citrus greening bacteria may not show symptoms for years following infection. Initial symptoms frequently include the appearance of yellow shoots on a tree. As the bacteria move within the tree, the entire canopy progressively develops a yellow color.

The most characteristic symptoms of citrus greening are a blotchy leaf mottle and vein yellowing that develop on leaves attached to shoots, providing the overall yellow appearance. These foliar symptoms may superficially resemble a zinc deficiency although the green and yellow contrast is not as vivid with greening as it is with zinc deficiency or another disease, citrus variegated chlorosis. Leaves with citrus greening have a mottled appearance that differs from nutrition-related mottling in that greening-induced mottling usually crosses leaf veins. Nutrition related mottles usually are found between or along leaf veins and leaves may be small and upright.

Fruit from diseased trees are small, often misshapen, and typically some green color remains on ripened fruit. On Mandarin orange, fruit may develop an uneven ripening such that they appear half orange and half yellow. This symptom is the origin of the common name "greening." Yields are almost minimal, and any developed fruit is rendered worthless due to small size, poor color, and bad taste.

It would be desirable to develop an effective chemical treatment method for the reduction of the incidence of insect-vectored bacterial infections such as citrus greening that stunt citrus plant development or kill plants. An effective chemical treatment would overcome the inadequacies of the known control measures and improve plant growth by providing systemic treatment, inducing plant self-defense, and controlling secondary infections such as fungal infections.

SUMMARY OF THE INVENTION

A method of treating a citrus plant is provided to reduce the incidence of one or more insect-vectored bacterial infections such as citrus greening. The method comprises the step of applying a treatment composition one or more times to the plant, wherein the treatment composition comprises an effective amount of aluminum tris(O-ethyl phosphonate), which is known in the art as a fungicide.

DETAILED DESCRIPTION OF THE INVENTION

Other than in the operating examples, or where otherwise indicated, all numbers expressing quantities of ingredients, reaction conditions and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of 1 to 10 is intended to include all sub-ranges between and including the recited minimum value of 1 and the recited maximum value of 10, that is, having a minimum value equal to or greater than 1 and a maximum value of equal to or less than 10.

As used herein, unless otherwise expressly specified, all numbers such as those expressing values, ranges, amounts or percentages may be read as if prefaced by the word "about", even if the term does not expressly appear. Any numerical range recited herein is intended to include all sub-ranges subsumed therein. Plural encompasses singular and vice versa; e. g., the singular forms "a," "an," and "the" include plural referents unless expressly and unequivocally limited to one referent.

With respect to the present invention, the phrase "effective amount" as used herein is intended to refer to an amount of an ingredient used such that a noticeable reduction in effects caused by insect-vectored bacterial infections is observed in plants treated using the method of the present invention, compared to plants that did not receive treatment.

The treatment method of the present invention comprises the step of applying a treatment composition one or more times to a citrus plant. The treatment composition comprises an effective amount of aluminum tris(O-ethyl phosphonate). A suitable source of aluminum tris(O-ethyl phosphonate) is available from Bayer CropScience as Aliette®.

The method of the present invention improves citrus plant growth by reducing the incidence of one or more insect-vectored bacterial infections, for example, citrus greening. Though not intending to be bound by theory, it is believed that phosphorous (phosphonic) acid has a direct and possibly an indirect effect on pathogens. It inhibits the metabolic process of oxidative phosphorylation. In addition, some evidence suggests that phosphorous acid and derivatives thereof stimulate a plant's natural defense response against pathogen attack. The phosphonate ion is highly systemic and fairly stable in plants. The fully systemic activity allows the treatment composition to be applied as foliar sprays, trunk applications, and soil/root treatments. Moreover, because of its systemic activity, upon application to the plant the phosphonate ion will be present in the plant phloem, where citrus greening bacteria infect the plant.

The treatment composition used in the treatment method of the present invention may further comprise one or more safeners or fungicides. Examples of suitable safeners include potassium carbonate, hydrated lime, or diammonium phosphate. Fungicides may be any of those known in the art; in particular, fungicides containing phosphorous acid and/or derivatives thereof. Examples of commercially available fungicides of this type include ProPhyt®, available from Helena Chemical Company, Phostrol®, available from NuFarm Americas, Inc., and Agri-Fos®, available from Agrichem Manufacturing Industries PTY.LTD.

The treatment composition may be applied to the plants in an amount of 2 to 7 lb/acre (0.91 to 3.18 kg/acre). It is typically applied in an amount of 5 lb/acre (2.27 kg/acre). The treatment composition may be applied using any of a variety of techniques, including combinations thereof. For example, the treatment composition may be applied one or more times to roots of plants during planting or transplanting, such as during transplanting of established plants; i. e., plants having at least two mature leaves. Application may be in-furrow and/or as a root dip. The treatment composition may additionally or alternatively be applied one or more times to foliage, trunks and/or roots of plants during plant growth. Methods of application include spraying, painting, and/or chemigation. In certain embodiments of the present invention, the treatment composition is initially applied one or more times to roots of plants during planting or transplanting in-furrow and/or as a root dip, and then subsequently applied one or more times to foliage, trunks and/or roots of plants during plant growth. In these scenarios, the treatment composition may be the same or different for each application.

In certain embodiments of the present invention, the treatment method may further include the step of applying additional compositions including one or more pesticides such as insecticides and/or fungicides. In particular, acibenzolar-S-methyl, phorate, aldicarb, chlorothalonil, acephate, tebuconazole, and/or neonicotinoids such as imidacloprid, thiacloprid, acetamiprid, clothianidin, nitenpyram, and thiamethoxam are suitable for use as additional treatment compositions. Each of these is available commercially and may be used in the method of the present invention in amounts conventionally recommended for their intended use.

Each of the treatment compositions used in the method of the present invention may independently be provided as emulsifiable concentrates, suspension concentrates, directly sprayable or dilutable solutions, coatable pastes, dilute emulsions, wettable powders, soluble powders, dispersible powders, dusts, granules or capsules. In addition to the components discussed above, they may each optionally include auxiliary agents commonly used in agricultural treatment formulations and known to those skilled in the art. Examples include wetting agents, dispersants, emulsifiers, penetrants, preservatives, antifreezes and evaporation inhibitors such as glycerol and ethylene or propylene glycol, sorbitol, sodium lactate, fillers, carriers, colorants including pigments and/or dyes, pH modifiers (buffers, acids, and bases), salts such as calcium, magnesium, ammonium, potassium, sodium, and/or iron chlorides, fertilizers such as ammonium sulfate and ammonium nitrate, urea, and defoamers.

Suitable defoamers include all customary defoamers including silicone-based and those based upon perfluoroalkyl phosphinic and phosphonic acids, in particular silicone-based defoamers, such as silicone oils, for example.

Defoamers most commonly used are those from the group of linear polydimethylsiloxanes having an average dynamic viscosity, measured at 25° C., in the range from 1000 to 8000 mPas (mPas=millipascal−second), usually 1200 to 6000 mPas, and containing silica. Silica includes polysilicic acids, meta-silicic acid, ortho-silicic acid, silica gel, silicic acid gels, kieselguhr, precipitated $SiO_2$, and the like.

Defoamers from the group of linear polydimethylsiloxanes contain as their chemical backbone a compound of the formula HO—[$Si(CH_3)_2$—O—]$_n$—H, in which the end groups are modified, by etherification for example, or are attached to the groups —$Si(CH_3)_3$. Non-limiting examples of defoamers of this kind are RHODORSIL® Antifoam 416 (Rhodia) and RHODORSIL® Antifoam 481 (Rhodia). Other suitable defoamers are RHODORSIL® 1824, ANTIMUSSOL 4459-2 (Clariant), Defoamer V 4459 (Clariant), SE Visk and AS EM SE 39 (Wacker). The silicone oils can also be used in the form of emulsions.

Whereas particular embodiments of this invention have been described above for purposes of illustration, it will be evident to those skilled in the art that numerous variations of the details of the present invention may be made without departing from the invention as defined in the appended claims.

What is claimed is:

1. A method of treating a citrus plant infected with one or more insect-vectored bacterial infections that result in citrus greening, comprising the step of applying a treatment composition to the infected plant to reduce the incidence of the insect-vectored bacterial infection that results in citrus greening, wherein the treatment composition comprises an effective amount of aluminum tris(O-ethyl phosphonate).

2. The method of claim 1, wherein the treatment composition further comprises one or more fungicides.

3. The method of claim 2, wherein the treatment composition further comprises one or more fungicides containing phosphorous acid and/or derivatives thereof.

4. The method of claim 1, wherein the treatment composition is applied in an amount of 5 lb/acre (2.27 kg/acre).

5. The method of claim 1, wherein the treatment composition is applied one or more times to roots of plants during planting or transplanting, in-furrow and/or as a root dip.

6. The method of claim 1, wherein the treatment composition is applied one or more times to foliage, trunks and/or roots of plants during plant growth.

7. The method of claim 6, wherein the treatment composition is applied to trunks.

8. The method of claim 6, wherein the treatment composition is applied to the plants by spraying, painting, and/or chemigation.

9. The method of claim 1, wherein the treatment composition is initially applied one or more times to roots of plants during planting or transplanting in-furrow and/or as a root dip, and then subsequently applied one or more times to foliage, trunks and/or roots of plants during plant growth, wherein the treatment composition may be the same or different for each application.

10. The method of claim 1, wherein the treatment composition is applied in an amount of 2 to 7 lb/acre (0.91 to 3.18 kg/acre).

11. The method of claim 2, wherein the treatment composition further comprises auxiliary agents.

12. The method of claim 1, wherein the treatment composition is applied one or more times to foliage of plants during plant growth.

13. The method of claim 1, wherein the treatment composition further comprises one or more safeners.

14. the method of claim 1, wherein the treatment composition further comprises one or more insecticides.

15. The method of claim 13, wherein the safener is selected from the group consisting of potassium carbonate, hydrated lime, and diammonium phosphate.

16. The method of claim 14, wherein the insecticide is selected from the group consisting of phorate, aldicarb, acephate, and neonicotinoid.

17. The method of claim 2 wherein the fungicide is selected from the group consisting of acibenzolar-S-methyl, chlorothalonil, and tebuconazole.

18. The method of claim 1, wherein the insect-vectored bacterial infection is *Candidatus Liberibacler asiaticus* vectored by the insect citrus psyllid.

19. The method of claim 1, wherein the treatment composition provides systemic treatment to the infected plant.

* * * * *